United States Patent [19]
Takaya et al.

[11] Patent Number: 4,558,047
[45] Date of Patent: Dec. 10, 1985

[54] 3,5-DI HYDROXY MORPHOLINE DERIVATIVES AND PHARMACEUTICAL COMPOSITIONS

[75] Inventors: Takao Takaya, Kawanishi; Zenzaburo Tozuka, Toyonaka, both of Japan

[73] Assignee: Fujisawa Pharmaceutical Co., Ltd., Osaka, Japan

[21] Appl. No.: 598,581

[22] Filed: Apr. 10, 1984

[30] Foreign Application Priority Data

Apr. 25, 1983 [GB] United Kingdom ............. 8311228

[51] Int. Cl.[4] ............... A61K 31/535; A61K 413/14

[52] U.S. Cl. ................... 514/229; 514/230; 514/234; 514/235; 514/237; 514/238; 514/239

[58] Field of Search ............. 544/118, 122, 123, 133, 544/134; 514/229, 230, 234, 235, 237, 238, 239

[56] References Cited

U.S. PATENT DOCUMENTS 3,542,776 11/1970 Dovonch et al. ............... 544/123

Primary Examiner—Robert W. Ramsuer
Attorney, Agent, or Firm—Oblon, Fisher, Spivak, McClelland & Maier

[57] ABSTRACT 3,5-Di hydroxy morpholine derivatives having antitumor activity and methods of preparation thereof, are disclosed.

18 Claims, No Drawings

3,5-DI HYDROXY MORPHOLINE DERIVATIVES AND PHARMACEUTICAL COMPOSITIONS

This invention relates to new morpholine derivatives. More particularly, this invention relates to new morpholine derivatives and pharmaceutically acceptable salt thereof which have antitumor activity, processes for preparation thereof, a pharmaceutical composition comprising the same and method of use thereof.

Accordingly, one object of this invention is to provide the new and useful morpholine derivatives and pharmaceutically acceptable salt thereof.

Another object of this invention is to provide processes for preparation of the morpholine derivatives and pharmaceutically acceptable salts thereof.

A further object of this invention is to provide a pharmaceutical composition comprising said morpholine derivative or pharmaceutically acceptable salt thereof as an antitumor agent.

Still further object of this invention is to provide a method of using said morpholine derivative or a pharmaceutically acceptable salt thereof for therapeutic treatment of cancer.

The morpholine derivatives of this invention are novel and represented by the following general formula (I):

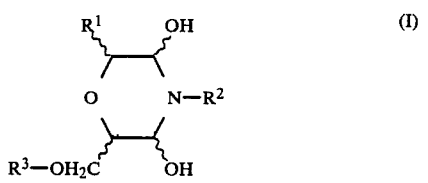

wherein
$R^1$ is a heterocyclic group selected from uracilyl, cytosinyl, hypoxanthinyl, adeninyl and thiazolyl, which may be substituted with halogen or carbamoyl,
$R^2$ is an N-containing unsaturated heterocyclic group which may be substituted with oxo or lower alkyl, and
$R^3$ is a hydrogen atom or a phosphono group.

Suitable examples and illustrations for the above definitions are explained in detail as follows.

The term "lower" is intended to mean 1 to 6 carbon atom(s) unless otherwise indicated.

The heterocyclic group for $R^1$ is uracilyl, cytosinyl, hypoxanthinyl, adeninyl or thiazolyl, and these heterocyclic groups may be substituted with halogen [e.g. fluorine, chlorine, bromine or iodine] or carbamoyl.

Suitable examples of the heterocyclic group having such substituent(s) may be halogenated heterocyclic group such as 5-fluorouracilyl, 5-chlorouracilyl, 5-bromouracilyl, 6-fluorouracilyl, 6-chlorouracilyl, 5-fluorocytosinyl, 5-chlorocytosinyl, 6-fluorocytosinyl, 2-fluorohypoxanthinyl, 8-chlorohypoxanthinyl, 8-chloroadeninyl, 2-chlorothiazolyl, carbamoyl substituted heterocyclic group such as 2-carbamoylthiazolyl, 4-carbamoylthiazolyl, or the like.

The N-containing unsaturated heterocyclic group for $R^2$ means unsaturated monocyclic or polycyclic group containing at least one nitrogen atom.

Suitable examples of the heterocyclic group for $R^2$ may be unsaturated 3- to 9-membered, preferably 5- or 6-membered, monocyclic heterocyclic group containing 1 to 4 nitrogen atom(s) such as pyrrolyl, imidazolyl, pyrazolyl, triazolyl, [e.g. 1H-1,2,3-triazolyl, 1H-1,2,4-triazolyl, 2H-1,2,3-triazolyl, 4H-1,2,4-triazolyl, etc.], tetrazolyl [e.g. 1H-tetrazolyl, 2H-tetrazolyl, etc.], pyridyl, pyrimidinyl, pyrazinyl, pyridazinyl or the like; unsaturated fused heterocyclic group containing 1 to 4 nitrogen atom(s) such as indolyl, benzimidazolyl, benzopyrazolyl, benzotriazolyl, purinyl or the like; unsaturated 3- to 9-membered, preferably 5- or 6-membered, monocyclic heterocyclic group containing 1 to 4 nitrogen atom(s) and 1 to 2 sulfur or oxygen atom(s) such as thiazolyl, isothiazolyl, thiadiazolyl [e.g. 1,2,3-thiadiazolyl, 1,2,4-thiadiazolyl, 1,3,4-thiadiazolyl, 1,2,5-thiadiazolyl, etc.], thiazolinyl, oxazolyl, isoxazolyl, oxadiazolyl [e.g. 1,2,4-oxadiazolyl, 1,3,4-oxadiazolyl, 1,2,5-oxadiazolyl, etc.] or the like.

The above-mentioned heterocyclic groups for $R^2$ may be substituted with oxo or lower alkyl [e.g. methyl, ethyl, propyl, isopropyl, butyl, isobutyl, sec-butyl, tert-butyl, pentyl, hexyl, etc.]. Suitable examples of the heterocyclic group having such substituent(s) may be 2-methylthiazolyl, 5-methyloxazolyl, hypoxanthinyl or the like.

Suitable pharmaceutically acceptable salts of the object compounds (I) are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine salt, ornithine salt, etc.], and the like.

The object compounds (I) and their salts of the present invention can be prepared by the following processes.

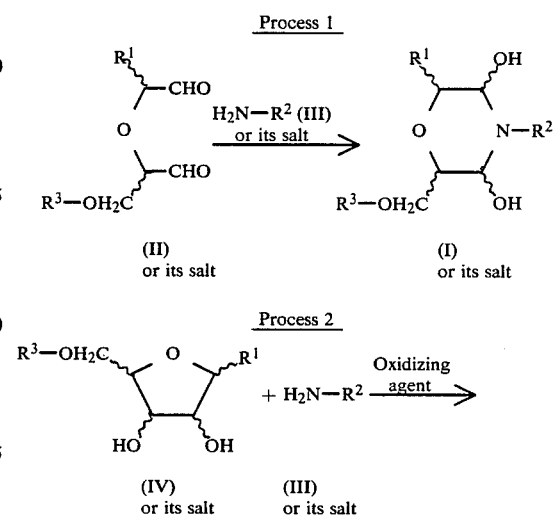

-continued

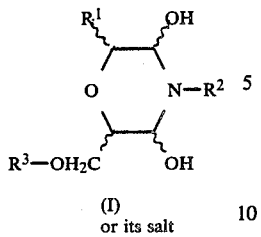

(I) or its salt

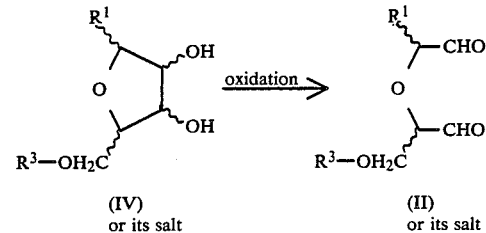

(IV) or its salt    (II) or its salt wherein $R^1$, $R^2$ and $R^3$ are each as defined above.

The processes for preparing the object compounds (I) and salts thereof are explained in detail in the following.

Process 1

The object compound (I) and its salt can be prepared by reacting a compound (II) or its salt with a compound (III) or its salt.

Suitable salts of the compounds (II) and (III) may be the same as those exemplified for the compound (I).

This reaction is usually carried out in a conventional solvent such as water, alcohol [e.g. methanol, ethanol, propanol, etc.], tetrahydrofuran, dioxane, dimethylformamide, dimethylsulfoxide or any other organic solvent which does not adversely influence the reaction, or a mixture thereof.

This reaction is preferably conducted in the presence of an acid such as inorganic acid [e.g. hydrochloric acid, hydrobromic acid, sulfuric acid, phosphoric acid, polyphosphoric acid, etc.], organic acid [e.g. acetic acid, trifluoroacetic acid, benzenesulfonic acid, toluenesulfonic acid, etc.] or the like. In case that the acid to be used in liquid, it can be also used as a solvent.

The reaction temperature is not critical, and the reaction is usually carried out at ambient temperature or under warming.

Process 2

The object compound (I) and its salt can be prepared by reacting a compound (IV) or its salt with a compound (III) or its salt in the presence of an oxidizing agent.

Suitable salts of the compounds (IV) and (III) may be the same as those exemplified for the compound (I).

Suitable oxidizing agent of this reaction may include conventional ones as used in oxidation of 1,2-diol function such as periodic acid or its salt [e.g. metaperiodic acid, sodium metaperiodate, potassium metaperiodate, paraperiodic acid, sodium paraperiodate, potassium paraperiodate, etc.], lead compound [e.g. lead tetraacetate, lead tetrabenzoate etc.], chromic acid or its salt [e.g. sodium dichromate, potassium dichromate, etc.] or the like.

This reaction is usually carried out in a conventional solvent such as water, alcohol [e.g. methanol, ethanol, t-butyl alcohol, etc.], dioxane, acetic acid or any other organic solvent which does not adversely influence the reaction, or a mixture thereof.

The reaction temperature is not critical, and the reaction is usually carried out under cooling to warming.

The starting compounds (II) include known compounds described in CARBOHYDRATE RESEARCH 1977, 54(1), 75-84, CANCER RESEARCH 1980, 40(3), 598-603, etc., and new compounds. The new starting compounds can be prepared by following method.

wherein $R^1$ and $R^3$ are each as defined above.

The compound (II) and its salt can be prepared by oxidizing a compound (IV) or its salt.

Suitable oxidizing agents of this reaction are the same as those exemplified in the explanation of Process 2.

This reaction is usually carried out in a conventional solvent such as water, alcohol [e.g. methanol, ethanol, t-butyl alcohol, etc.], dioxane, acetic acid, or a mixture thereof, and these solvents may be selected according to the kind of the oxidizing agent to be used. The reaction temperature is not critical, and the reaction is usually carried out under cooling to warming.

The compound (II) can be isolated by a conventional manner such as ion-exchange resin column, lyophilization or the like, but it can optionally be used in the next step, i.e. Process 1, without isolation.

It is to be noted that each of the object compound (I) and the starting compounds (II), (III) and (IV) include one or more stereoisomers due to asymmetric carbon atoms in the molecule and tautomers, and all of such isomers of the compound (I), (II), (III) and (IV) are included within the scope of this invention.

The new morpholine derivatives (I) and pharmaceutically acceptable salts thereof possess an antitumor activity, and are useful for a therapeutic treatment of cancer.

For the purpose of showing pharmacological activity of the object compounds (I), test data on antitumor activity are illustrated in the following.

Test Method

Six male B D $F_1$ mice, aged more than 6 weeks, weighing 22.6 g to 25.9 g were used per group. Lymphocytic Leukemia P388 was transferred every 6 or 7 days in DBA/2 mice by intraperitoneal inoculation of ascites cells. Test compounds were dissolved in phosphate buffer serum (PBS). After 24 hours of the inoculation of Leukemia cells to the test mice, test compound was administered intraperitoneally in doses of 32, 56, 100, 320 mg/kg, respectively, in each medicated group (PBS only in the control group) once a day for 4 days. Antitumor activity of the test compound was evaluated by the increase in life-span over control (ILS=T/C×T/C×100—100) in leukemias, wherein T is medium survival time (MST) of the medicated group, and C is medium survival time of control group.

Test Result

The test results are shown in the following table 1.

TABLE 1

| Test Compound (Example No.) | Dose (mg/kg) | ILS (%) |
|---|---|---|
| Example 1 | 32 | 55 |
|  | 100 | 100 |
| Example 2 | 100 | 75 |
| Example 3 | 32 | 30 |

TABLE 1-continued

| Test Compound (Example No.) | Dose (mg/kg) | ILS (%) |
|---|---|---|
|  | 100 | 85 |
|  | 320 | 300 |
| Example 4 | 32 | 30 |
|  | 100 | 60 |
|  | 320 | 90 |
| Example 6 | 32 | 30 |
|  | 100 | 80 |
| Example 7 | 32 | 60 |
|  | 100 | 80 |
| Example 8 | 32 | 45 |
|  | 100 | 70 |
| Example 12 | 32 | 46 |
|  | 100 | 67 |
| Example 14 | 32 | 60 |
|  | 100 | 85 |
|  | 320 | 295 |
| Example 16 | 32 | 55 |
|  | 100 | 80 |

As being apparent from the above test results, the object compounds (I) of the present invention are useful as an antitumor agent.

For therapeutic administration, the object compound (I) of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as capsule, tablet, dragee or suppository, or in a liquid form such as solution, suspension or emulsion. If needed, there may be included in the above preparation auxiliary substance, stabilizing agent, wetting or emulsifying agent, buffer or any other commonly used additives.

The effective ingredient may usually be administered with a unit dose of 1.0 mg/kg to 1000 mg/kg, 1 to 4 times a day. However, the above dosage may be increased or decreased according to age, weight, conditions of the patient or the administering method.

The following examples are given only for the purpose of illustrating the present invention in more detail.

EXAMPLE 1

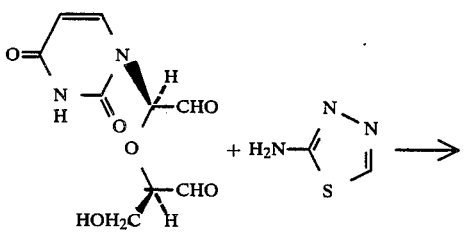

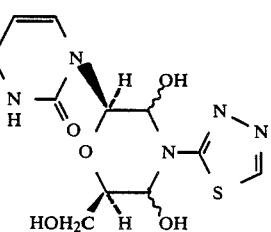

[R-(R*, R*)]-α-(1-Formyl-2-hydroxyethoxy)-3,4-dihydro-2,4-dioxo-1(2H)-pyrimidineacetaldehyde, (uridinedialdehyde), (2.42 g) was dissolved in a mixture of methanol (50 ml) and water (50 ml). To the solution was added 2-amino-1,3,4-thiadiazole (1.00 g). The mixture was stirred at ambient temperature for four hours and evaporated in vacuo. The residue was triturated with acetone to give 1-[(2R, 6R)-3,5-dihydroxy-6-hydroxymethyl-4-(1,3,4-thiadiazol-2-yl)morpholin-2-yl]-uracil (3.0 g).

mp 170°–180° C. (dec.)

IR (Nujol): 3200, 1690 cm$^{-1}$.

NMR (D$_2$O)δ: 3.6–4.5 (3H, m), 5.0–5.7 (2H, m), 5.7–6.2 (2H, m), 7.1–8.1 (1H, m), 8.6–9.0 (1H, m).

EXAMPLE 2

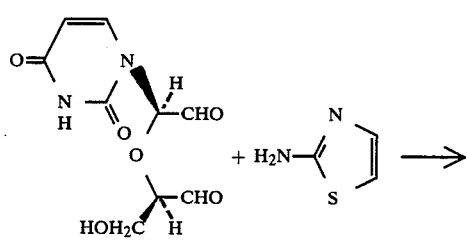

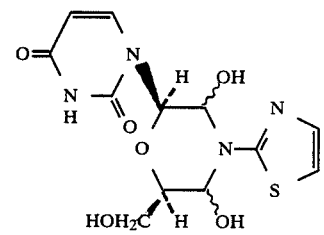

[R-(R*, R*)]-α-(1-Formyl-2-hydroxyethoxy)-3,4-dihydro-2,4-dioxo-1(2H)pyrimidineacetaldehyde, (uridinedialdehyde), (6.05 g) was dissolved in water (25 ml). To a solution was added 2-aminothiazole (2.50 g). The mixture was stirred at ambient temperature overnight to give a clear solution. The solution was subjected to column chromatography on HP-20 resine, which was eluted with water and then 50% aqueous acetone. The elution was condenced in vacuo and lyophilized to give white powder of 1-[(2R, 6R)-3,5-dihydroxy-6-hydroxymethyl-4-(2-thiazolyl)morpholin-2-yl]uracil (8.09 g).

mp 130°–135° C. (dec.)

IR (Nujol): 3250, 1690 cm$^{-1}$.

NMR (D$_2$O)δ: 3.6–4.5 (3H, m), 5.1–5.8 (2H, m), 5.8–6.2 (2H, m), 6.7–7.5 (2H, m), 7.7–8.2 (1H, m).

EXAMPLE 3

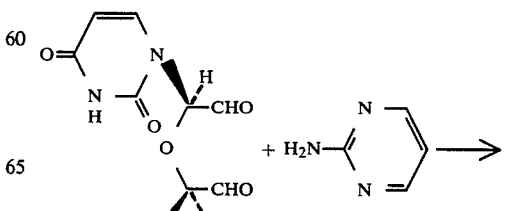

-continued

[R-(R*, R*)]-α-(1-Formyl-2-hydroxyethoxy)-3,4-dihydro-2,4-dioxo-1(2H)-pyrimidineacetaldehyde, (uridinedialdehyde), (6.05 g) was dissolved in water (25 ml). To the solution was added 2-aminopyrimidine (2.38 g). The mixture was stirred at ambient temperature for eight hours to give a clear solution. The solution was lyophilized to give white powder of 1-[(2R, 6R)-3,5-dihydroxy-6-hydroxymethyl-4-(2-pyrimidinyl)morpholin-2-yl]uracil (8.40 g).

mp 155°–160° C. (dec.)

IR (Nujol): 3300, 1690, 1580 cm$^{-1}$.

NMR (D$_2$O)δ: 3.7–4.4 (3H, m), 5.1–5.5 (1H, m), 5.5–6.4 (3H, m), 6.7–7.2 (1H, m), 7.7–8.2 (1H, m), 8.2–8.7 (2H, m).

EXAMPLE 4

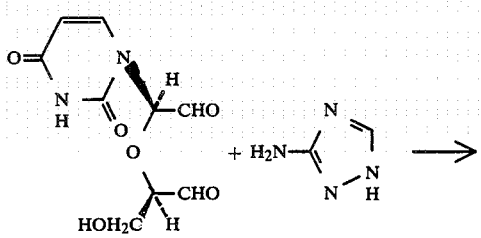

[R-(R*, R*)]-α-(1-Formyl-2-hydroxyethoxy)-3,4-dihydro-2,4-dioxo-1(2H)-pyrimidineacetaldehyde, (uridinedialdehyde), (4.84 g) was dissolved in a mixture of methanol (100 ml) and water (100 ml). To the solution was added 3-amino-1H-1,2,4-triazole (1.68 g). The mixture was stirred at ambient temperature for five hours and evaporated in vacuo. The residue was triturated with acetone to give 1-[(2R, 6R)-3,5-dihydroxy-6-hydroxymethyl-4-(1,2,4-triazol-3-yl)morpholin-2-yl]uracil (6.25 g).

mp 210° C. (dec.)

IR (Nujol): 3200, 1680 cm$^{-1}$.

NMR (D$_2$O)δ: 3.7–4.5 (3H, m), 5.0–6.5 (4H, m), 7.7–8.5 (2H, m).

EXAMPLE 5

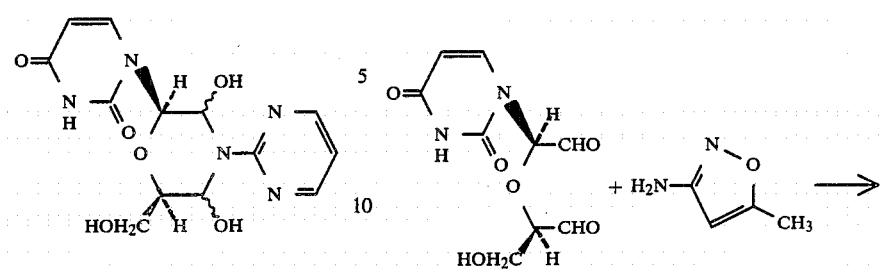

[R-(R*, R*)]-α-(1-Formyl-2-hydroxyethoxy)-3,4-dihydro-2,4-dioxo-1(2H)pyrimidineacetaldehyde, (uridinedialdehyde), (4.0 g) was dissolved in a mixture of methanol (30 ml) and water (30 ml). To the solution was added 3-amino-5-methylisoxazole (1.62 g). The mixture was stirred at ambient temperature for five hours and evaporated in vacuo. The residue was triturated with acetone to give 1-[(2R, 6R)-3,5-dihydroxy-6-hydroxymethyl-4-(5-methylisoxazol-3-yl)morpholin-2-yl]uracil (4.2 g).

mp 163°–167° C. (dec.)

IR (Nujol): 3300, 1690, 1620 cm$^{-1}$.

NMR (D$_2$O)δ: 2.1–2.4 (3H, m), 3.6–4.5 (3H, m), 4.9–5.5 (2H, m), 5.5–6.2 (3H, m), 7.7–8.2 (1H, m).

EXAMPLE 6

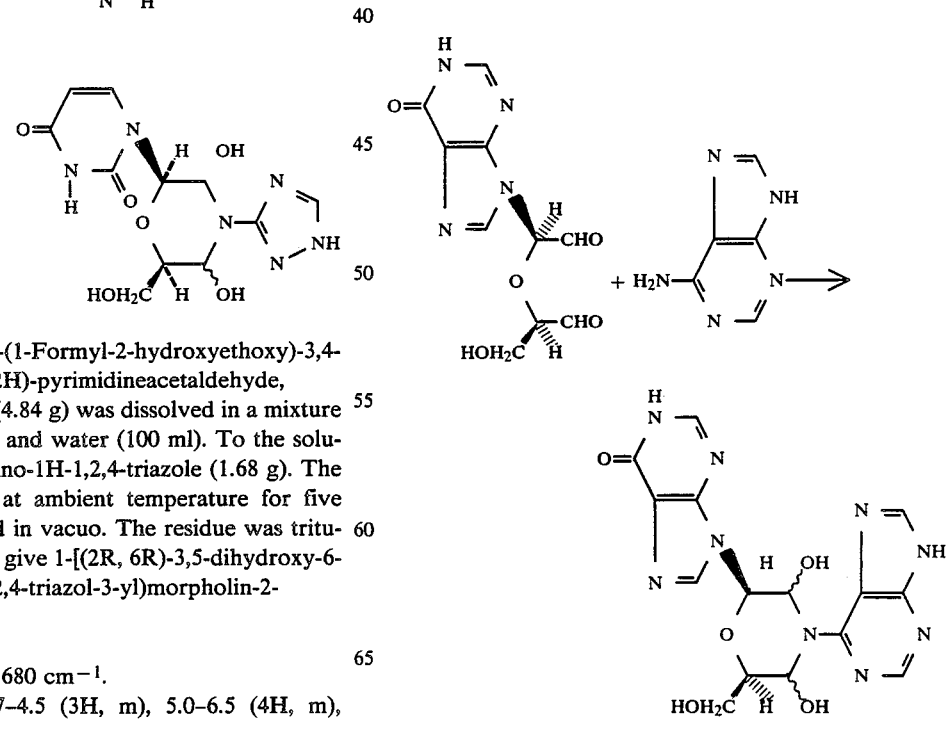

[R-(R*, R*)]-α-(1-Formyl-2-hydroxyethoxy)-1,6-dihydro-6-oxo-9H-purine-9-acetaldehyde, (inosinedialdehyde), (2.66 g) was dissolved in a mixture of methanol (100 ml) and water (100 ml). To the solution was added adenine (1.35 g). The mixture was stirred at ambient temperature for one day and filtered. The filtrate was evaporated in vacuo at 35° C. The residue was triturated with acetone to give 9-[(2R, 6R)-3,5-dihydroxy-6-hydroxymethyl-4-(6-purinyl)morpholin-2-yl]hypoxanthine (3.20 g).

mp 125°–135° C. (dec.)

IR (Nujol): 3150, 1690, 1590 cm⁻¹.

NMR (D₂O)δ: 3.6–4.5 (3H, m), 5.0–6.5 (3H, m), 8.0–8.7 (4H, m)

EXAMPLE 7

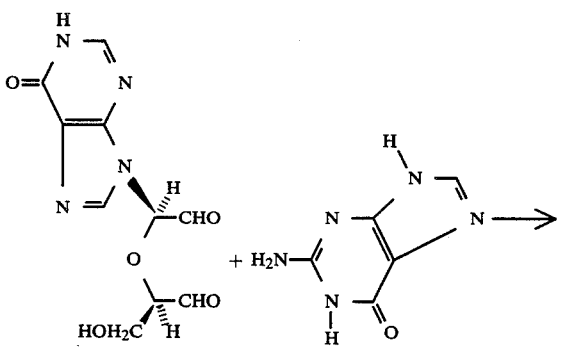

[R-(R*, R*)]-α-(1-Formyl-2-hydroxyethoxy)-1,6-dihydro-6-oxo-9H-purine-9-acetaldehyde, (inosinedialdehyde), (1.33 g) was dissolved in a mixture of methanol (300 ml) and water (300 ml). To the solution was added guanine (0.76 g). The mixture was stirred at ambient temperature for three days and filtered. The filtrate was evaporated in vacuo at 35° C. The residue was triturated with acetone to give 9-[(2R, 6R)-3,5-dihydroxy-6-hydroxymethyl-4-(2-hypoxanthinyl)morpholin-2-yl]hypoxanthine (2.20 g).

mp 115°–120° C. (dec.)

IR (Nujol): 1310, 1680, 1580 cm⁻¹.

NMR (D₂O)δ: 3.7–4.5 (3H, m), 5.0–6.3 (3H, m), 8.2–8.8 (3H, m).

EXAMPLE 8

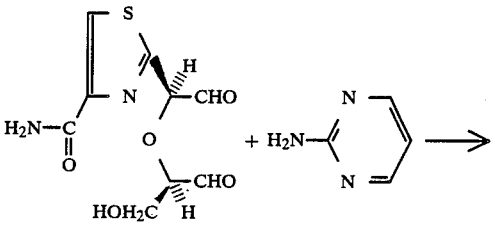

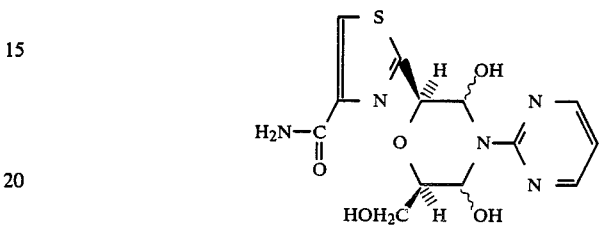

[R-(R*, R*)]-α-(1-Formyl-2-hydroxyethoxy)-4-carbamoyl-2-1,3-thiazoleacetaldehyde (1.10 g) was dissolved in water (30 ml). To the solution was added 2-aminopyrimidine (0.41 g). The mixture was stirred at ambient temperature for five hours to give a clear solution. The solution was lyophilized to give 2-[(2R, 6R)-3,5-dihydroxy-6-hydroxymethyl-4-(2-pyrimidinyl)morpholin-2-yl]-4-carbamoylthiazole (1.50 g).

mp 105°–110° C. (dec.)

IR (Nujol): 3320, 1680, 1630, 1580 cm⁻¹.

NMR (D₂O)δ: 3.5–4.2 (3H, m), 4.5–6.0 (3H, m), 6.7–7.1 (1H, m), 8.1–8.8 (3H, m).

EXAMPLE 9

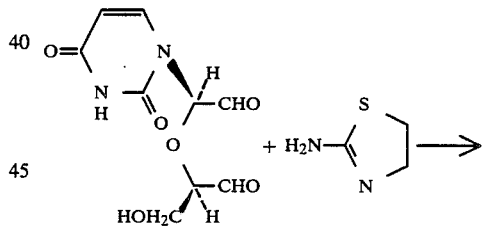

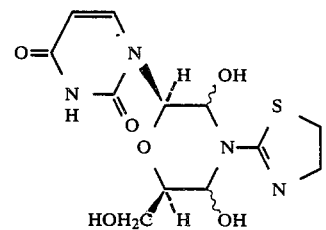

[R-(R*, R*)]-α-(1-Formyl-2-hydroxyethoxy)-3,4-dihydro-2,4-dioxo-1(2H)-pyrimidineacetaldehyde, (uridinedialdehyde), (2.4 g) was dissolved in water (10 ml). To the solution was added 2-amino-2-thiazoline (1.2 g). The mixture was stirred at ambient temperature overnight. An insoluble material was filtered off. The filtrate was evaporated in vacuo. The residue was triturated with acetone to give 1-[(2R, 6R)-3,5-dihydroxy-6-hydroxymethyl-4-(2-thiazolin-2-yl)morpholin-2-yl]uracil (0.98 g).

IR (Nujol): 3250, 1680 cm$^{-1}$.

NMR (DMSO-d$_6$-D$_2$O)δ: 2.7–4.5 (7H, m), 4.5–6.0 (3H, m), 7.3–8.1 (2H, m).

EXAMPLE 10

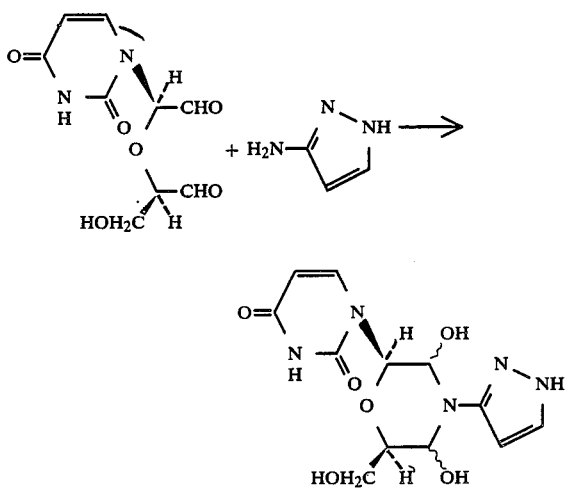

[R-(R*, R*)]-α-(1-Formyl-2-hydroxyethoxy)-3,4-dihydro-2,4-dioxo-1(2H)-pyrimidineacetaldehyde, (uridinedialdehyde), (2.4 g) was dissolved in water (10 ml). To the solution was added 3-aminopyrazole (0.83 g). The mixture was stirred at ambient temperature overnight. The precipitates were filtered and air-dried to give 1-[(2R, 6R)-3,5-dihydroxy-6-hydroxymethyl-4-(3-pyrazolyl)morpholin-2-yl]uracil (1.25 g).

IR (Nujol): 3250, 1680 cm$^{-1}$.

NMR (DMSO-d$_6$-D$_2$O)δ: 2.7–4.6 (3H, m), 4.6–6.5 (3H, m), 7.0–8.0 (4H, m).

EXAMPLE 11

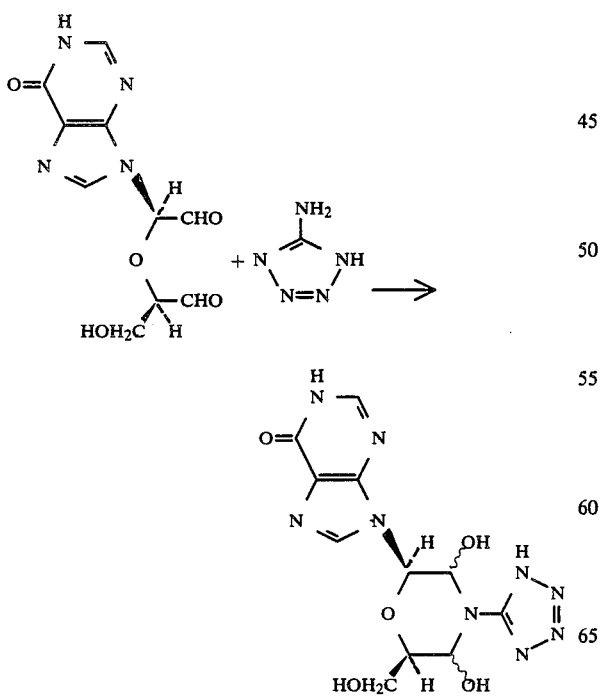

[R-(R*, R*)]-α-(1-Formyl-2-hydroxyethoxy)-1,6-dihydro-6-oxo-9H-purine-9-acetaldehyde, (inosine-dialdehyde), (2.6 g) was dissolved in water (25 ml). To the solution was added 5-aminotetrazole (1.03 g) and stirred at ambient temperature overnight. The reaction mixture was subjected to column chromatography on macroporous non-ionic adsorption resin (Diaion HP-20, prepared by Mitsubishi Chem. Ind. Ltd.). The column was eluted with water.

The eluate was lyophilized to give 9-[(2R, 6R)-3,5-dihydroxy-6-hydroxymethyl-4-(tetrazol-5-yl)-morpholin-2-yl]hypoxanthine (2.0 g).

IR (Nujol): 3200, 1690 cm$^{-1}$.

NMR (D$_2$O)δ: 3.6–4.7 (3H, m), 5.0–6.3 (3H, m), 8.0–8.8 (2H, m).

EXAMPLE 12

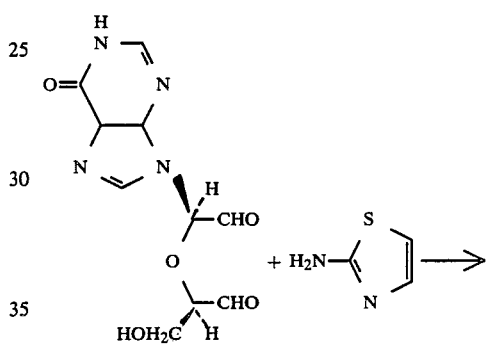

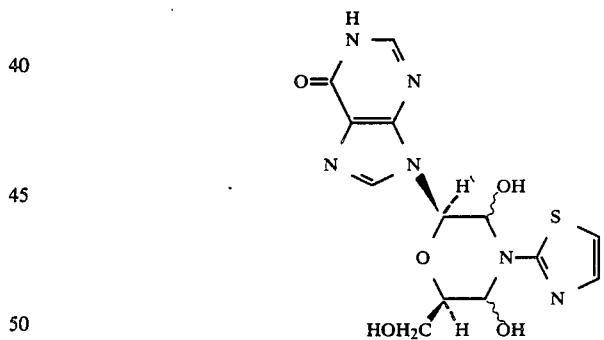

[R-(R*, R*)]-α-(1-Formyl-2-hydroxyethoxy)-1,6-dihydro-6-oxo-9H-purine-9-acetaldehyde, (inosine-dialdehyde), (2.6 g) was dissolved in water (30 ml). To the solution was added 2-aminothiazole (1.0 g). The solution was adjusted at pH 5.0 with dilute hydrochloric acid and stirred at ambient temperature overnight. The precipitate was collected by filtration, washed with acetone and air-dried to give 9-[(2R, 6R)-3,5-dihydroxy-6-hydroxymethyl-4-(2-thiazolyl)morpholin-2-yl]hypoxanthine (2.2 g).

IR (Nujol): 3200, 1700 cm$^{-1}$.

NMR (DMSO—d$_6$—D$_2$O)δ: 3.5–5.2 (3H, m), 5.2–6.5 (3H, m), 6.8–7.5 (2H, m), 8.0–8.3 (2H, m).

EXAMPLE 13

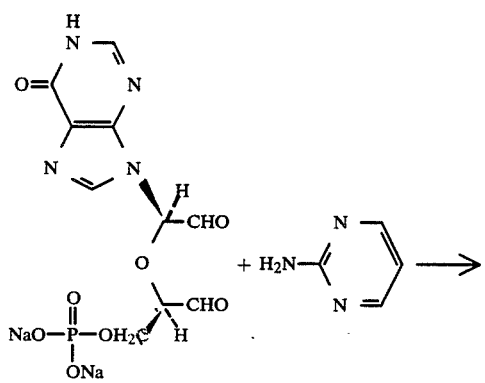

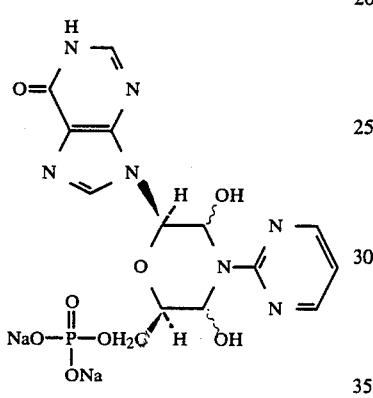

[R-(R*, R*)]-α-(1-Formyl-2-disodiophosphonoethoxy)-1,6-dihydro-6-oxo-9H-purine-9-acetaldehyde, (1.95 g) was dissolved in water (50 ml). To the solution was added 2-aminopyrimidine (0.48 g). The solution was stirred at ambient temperature for 1.3 hours and evaporated in vacuo. The residue was triturated with acetone and dried over phosphorus pentoxide in vacuo to give 9-[(2R, 6R)-3,5-dihydroxy-6-disodiophosphonomethyl-4-(pyrimidin-2-yl)morpholin-2-yl]hypoxanthine (2.1 g).

IR (Nujol): 3200, 1690, 1585 cm$^{-1}$.

NMR (D$_2$O)δ: 3.5–4.7 (3H, m), 5.2–6.5 (3H, m), 6.6–7.1 (1H, m), 7.9–8.8 (4H, m).

EXAMPLE 14

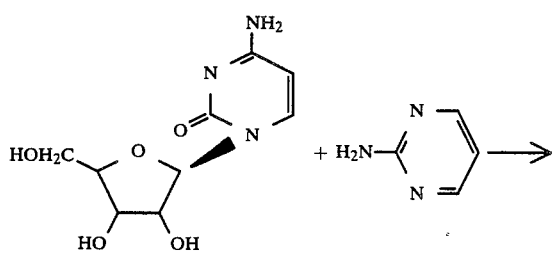

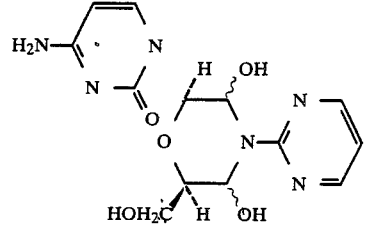

To a solution of cytidine (2.43 g) and 2-aminopyrimidine (0.95 g) in water (15 ml) was added sodium metaperiodate (2.13 g) at 15° C. The solution was stirred at ambient temperature for four hours. To the reaction mixture was added methanol (20 ml). A precipitate was filtered off and the filtrate was condenced in vacuo. The condenced solution was lyophilized to give white powder of 1-[(2R, 6R)-3,5-dihydroxy-6-hydroxymethyl-4-(2-pyrimidinyl)morpholin-2-yl]cytosine (3.20 g).

mp 145°–150° C. (dec.)

IR (Nujol): 3250, 1640, 1580 cm$^{-1}$.

NMR (D$_2$O)δ: 3.7–4.3 (3H, m), 5.1–5.5 (1H, m), 5.5–6.4 (3H, m), 6.7–7.2 (1H, m), 7.7–8.2 (1H, m), 8.2–8.7 (2H, m).

EXAMPLE 15

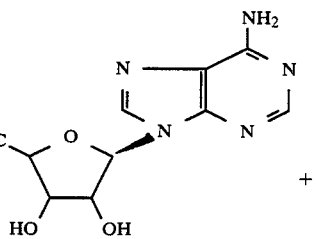

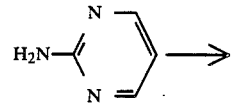

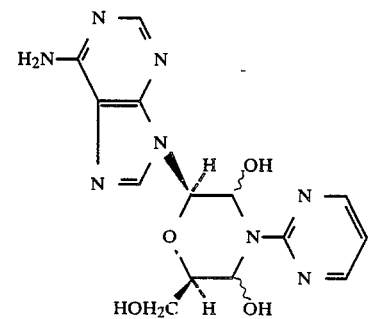

A solution of sodium metaperiodate (2.13 g) in water (25 ml) was added to a suspension of adenosine (2.67 g) and 2-aminopyrimidine in water (25 ml) at 15° C. The mixture was stirred at ambient temperature for five hours. To the reaction mixture was added methanol (50 ml). A precipitate was filtered off and the filtrate was evaporated in vacuo at 35° C. The residue was triturated with acetone to give 9-[(2R, 6R)-3,5-dihydroxy-6-hydroxymethyl-4-(2-pyrimidinyl)morpholin-2-yl]adenine (3.64 g).

mp 155°–160° C. (dec.)

IR (Nujol): 3350, 3200, 1640, 1580 cm$^{-1}$.
NMR (D$_2$O)δ: 3.5–4.33 (3H, m), 5.0–6.2 (3H, m), 6.5–7.1 (1H, m), 8.0–8.8 (4H, m).

EXAMPLE 16

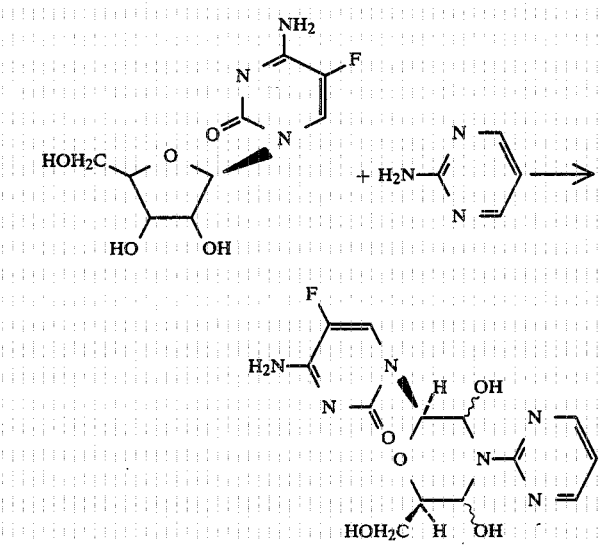

To a solution of 5-fluorocytidine (2.42 g) and 2-aminopyrimidine (0.95 g) in water (50 ml) was added sodium metaperiodate (2.13 g) under cooling with an ice-water bath. The solution was stirred at ambient temperature for 8 hours. To the reaction mixture was added methanol (50 ml). The precipitate was filtered off and the filtrate was evaporated in vacuo. The residue was triturated with acetone and air-dried to give 1-[(2R, 6R)-3,5-dihydroxy-6-hydroxymethyl-4-(2-pyrimidinyl)-morpholin-2-yl]-5-fluorocytosine (2.3 g).

IR (Nujol): 3300, 1670, 1580 cm$^{-1}$.
NMR (D$_2$O)δ: 3.6–4.5 (3H, m), 5.0–7.0 (4H, m), 7.5–7.7 (1H, m), 7.7–8.3 (2H, m).

What we claim is:

1. A compound of the formula:

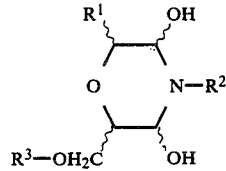

wherein
R$^1$ is a heterocyclic group selected from uracilyl, cytosinyl, hypoxanthinyl, adeninyl and thiazolyl, which may be substituted with halogen or carbamoyl, R$^2$ is an N-containing unsaturated heterocyclic group which may be substituted with oxo or lower alkyl, and
R$^3$ is a hydrogen atom or a phosphono group, and pharmaceutically acceptable salts thereof.

2. A compound of claim 1, wherein
R$^2$ is an N-containing unsaturated heterocyclic group selected from 5 membered ring, 6 membered ring and fused ring comprising 5 and 6 membered rings, which may be substituted with oxo or lower alkyl.

3. A compound of claim 2, wherein
R$^2$ is an N-containing unsaturated heterocyclic group selected from thiadiazolyl, thiazolyl, thiazolinyl, isoxazolyl, pyrazolyl, triazolyl, tetrazolyl, pyrimidinyl, purinyl and hypoxanthinyl.

4. A compound of claim 3, wherein
R$^2$ is thiadiazolyl, thiazolyl, tetrazolyl, pyrimidinyl, purinyl or hypoxanthinyl.

5. A compound of claim 4, wherein
R$^1$ is uracilyl, cytosinyl, hypoxanthinyl, thiazolyl, in which these groups may be substituted with halogen or carbamoyl.

6. A compound of claim 5, wherein
R$^1$ is uracilyl optionally substituted with halogen.

7. A compound of claim 6, which is
1-[(2R, 6R)-3,5-dihydroxy-6-hydroxymethyl-4-(2-pyrimidinyl)morpholin-2-yl]uracil.

8. A compound of claim 6, which is
1-[(2R, 6R)-3,5-dihydroxy-6-hydroxymethyl-4-(1,2,4-triazol-3-yl)morpholin-2-yl]uracil.

9. A compound of claim 6, which is
1-[(2R, 6R)-3,5-dihydroxy-6-hydroxymethyl-4-(1,3,4-thiadiazol-2-yl)morpholin-2-yl]uracil.

10. A compound of claim 5, wherein
R$^1$ is cytosinyl optionally substituted with halogen.

11. A compound of claim 10, which is
1-[(2R, 6R)-3,5-dihydroxy-6-hydroxymethyl-4-(2-pyrimidinyl)morpholin-2-yl]cytosine.

12. A compound of claim 10, which is
1-[(2R, 6R)-3,5-dihydroxy-6-hydroxymethyl-4-(2-pyrimidinyl)morpholin-2-yl]-5-fluorocytosine.

13. A compound of claim 5, wherein
R$^1$ is thiazolyl optionally substituted with carbamoyl.

14. A compound of claim 13, which is
2-[(2R, 6R)-3,5-dihydroxy-6-hydroxymethyl-4-(2-pyrimidinyl)morpholin-2-yl]-4-carbamoylthiazole.

15. A compound of claim 5, wherein
R$^1$ is hypoxanthinyl.

16. A compound of claim 15, which is
9-[(2R, 6R)-3,5-dihydroxy-6-hydroxymethyl-4-(6-purinyl)morpholin-2-yl]hypoxanthine.

17. A compound of claim 15, which is
9-[(2R, 6R)-3,5-dihydroxy-6-hydroxymethyl-4-(2-hypoxanthinyl)morpholin-2-yl]hypoxanthine.

18. A pharmaceutical composition comprisng a compound of claim 1, as an effective ingredient, in association with a pharmaceutically acceptable, substantially nontoxic carrier or excipient.

* * * * *